United States Patent [19]

Pless et al.

[11] Patent Number: 5,456,706
[45] Date of Patent: Oct. 10, 1995

[54] CARDIAC DEFIBRILLATION LEAD HAVING DEFIBRILLATION AND ATRIAL SENSING ELECTRODES

[75] Inventors: Benjamin D. Pless, Menlo Park; Drew A. Hoffmann, Los Gatos; Michael B. Sweeney, Menlo Park; M. Elizabeth Bush, Fremont; Steven M. Mitchell, Atherton, all of Calif.

[73] Assignee: Ventritex, Inc., Sunnyvale, Calif.

[21] Appl. No.: 177,293

[22] Filed: Jan. 4, 1994

[51] Int. Cl.⁶ .................................................. A61H 1/39
[52] U.S. Cl. ........................................... 607/122; 128/642
[58] Field of Search .......................... 128/642; 607/119, 607/122, 123, 125, 126, 130, 4–6

[56] References Cited

U.S. PATENT DOCUMENTS

| Re. 27,757 | 9/1973 | Mirowski | 128/419 |
|---|---|---|---|
| 3,825,015 | 7/1974 | Berkovits | 128/404 |
| 4,603,705 | 8/1986 | Speicher et al. | 607/122 |
| 4,630,611 | 12/1986 | King | 128/642 |
| 4,662,377 | 5/1987 | Heilman et al. | 128/419 |
| 4,953,551 | 9/1990 | Mehra et al. | 128/419 |
| 5,007,422 | 4/1991 | Pless et al. | 128/419 |
| 5,007,436 | 4/1991 | Smits | 128/786 |
| 5,144,960 | 9/1992 | Mehra et al. | 128/786 |
| 5,209,229 | 5/1993 | Gilli | 128/419 |
| 5,243,980 | 9/1993 | Mehra | 607/6 |
| 5,304,139 | 4/1994 | Adams et al. | 607/122 |

OTHER PUBLICATIONS

"Effect of Bipole Configuration on Atrial Electrograms During Atrial Fibrillation", Baerman, et al *PACE*, vol. 13, Jan. 1990, pp. 78–87.

"Implantable Transvenous Cardioverter–Defibrillators" Hardy, et al., *Circulation*, vol. 87, No. 4, Apr. 1993.

"Clinical Evaluation of VDD Pacing with a Unipolar Single–Pass Lead" Cornacchia, et al., *PACE*, vol. 12, Apr. 1989, Part I, pp. 604–618.

"Reliable Sensing of Human Atrial Fibrillation" Ruetz, et al., *PACE*, vol. 16, Apr. 1993, Part II, p. 902.

"Dual–chamber Rhythm Classifier for Implantable Cardioverter Defibrillators" Murphy, et al., *PACE*, vol. 16, Apr. 1993, Part II, p. 928.

"Initial Experience on the First Single Lead VDDR Pacing System : Assessment using Cardiopulmonary Exercise", Lau, et al., *PACE*, vol. 16, Jul. 1993, Part II, p. 1586.

Advertisement from Medica Electronic Devices International Co. (M.E.D.I.CO. Italia) in *Pace*, Oct. 1993, vol. 16, No. 10.

"Enguard™ Non–Thoracotomy Endocardial Defibrillation Lead System", Telectronics Pacing Systems, 4 pages.

*Primary Examiner*—William E. Kamm
*Assistant Examiner*—Marianne Parker
*Attorney, Agent, or Firm*—Steven M. Mitchell; Mark J. Meltzer; M. Elizabeth Bush

[57] ABSTRACT

A lead for use with an implantable cardioverter/defibrillator system is disclosed. In the preferred embodiment, the lead combines a right ventricular endocardial electrode, a superior vena cava electrode and one or more atrial sensing electrodes on a single catheter lead. The distal end of the lead is transvenously implanted, typically through an incision in the cephalic or subclavian vein. The proximal end of the lead is then tunneled below the fascia to the location of the pulse generator. Ventricular sensing and/or pacing electrode(s) may also be included at the distal end of the combined lead to provide ventricular intracardiac electrogram sensing and bradycardia pacing.

14 Claims, 6 Drawing Sheets

CARDIAC DEFIBRILLATION LEAD HAVING DEFIBRILLATION AND ATRIAL SENSING ELECTRODES

FIELD OF THE INVENTION

The present invention relates generally to implantable cardiac stimulation devices, and more specifically to a novel defibrillation lead system for use with an implantable defibrillator.

BACKGROUND OF THE INVENTION

Implantable cardioverter/defibrillators (ICDs) have been under development since at least the late 1960's. Such a device is described in U.S. Pat. No. Re. 27,757 to Mirowski. A more advanced system is disclosed in U.S. Pat. No. 5,007,422 to Pless et al. which is assigned to the assignee of the present invention and which is incorporated herein by reference. While the technology of ICDs has advanced significantly, a need still exists for improved sensing.

As used herein, the term defibrillation generally may be defined as the correction of either ventricular tachycardia or ventricular fibrillation by the discharge of electrical energy into the heart (0.1–40 joules when discharged through internal electrodes). Ventricular tachycardia is an abnormally rapid heart rate (120–180 beats per minute) originating in the ventricles which is generally regular in periodicity and oftentimes is life threatening to the patient. Ventricular fibrillation is generally a more rapid heartbeat disorder, disorganized and irregular, or non-periodic, and is fatal unless corrected within minutes. This can be accomplished by the discharge of electrical energy through the heart.

Detection and incorrect diagnosis of atrial fibrillation or supraventricular tachycardia by ICDs is a frequent cause of inappropriate shocks. These are heart rhythms generated in the atria which generally do not require defibrillator shocks for treatment. Methods which have been devised to reject these rhythms are often too complex to be incorporated in ICDs using currently available technology, or compromise sensitivity to ventricular tachycardia or ventricular fibrillation. Addition of atrial sensing to an ICD could significantly improve specificity of ventricular tachyarrhythmia detection.

Many different types of electrode systems have been suggested over the years. The above mentioned Mirowski patent describes an electrode arrangement whereby one electrode is formed on the distal end of an intravascular catheter that is positioned within the right ventricle and a second electrode is positioned on the surface of the chest or sutured under the skin of the chest wall or directly to the ventricular myocardium. Mehra et al. disclose a system in U.S. Pat. No. 4,953,551 wherein a first catheter mounted electrode is located in the apex of the right ventricle (RV) and a second electrode carried on the same catheter is located in the superior vena cava (SVC). For some patients, an additional electrode is required to reduce the defibrillation threshold to a safe level. This electrode is a patch electrode which is located subcutaneously outside the chest cavity. This subcutaneous patch electrode is typically provided when the arrangement of the RV electrode and the SVC electrode has a defibrillation threshold (DFT) at the time of implant which is too high to be considered safe and effective. A similar system is described in U.S. Pat. No. 4,662,377 to Hellman et al. Still other systems provide a separate catheter for the SVC electrode along with the catheter for the RV electrode and the subcutaneous patch electrode.

Many defibrillation lead systems include a pacing electrode on the distal tip of the catheter, distal to the RV electrode. In this configuration, the distal tip electrode and the RV electrode are sometimes paired for pacing and sensing functions but are electrically isolated for cardioversion and defibrillation. U.S. Pat. No. 4,603,705 to Speicher et al. describes such a lead. On the other hand, a separate ring electrode may be provided to be paired with the pacing tip electrode. U.S. Pat. No. 5,209,229 to Gilli describes an atrial J and a ventricular endocardial lead, each including tip and ring pacing electrodes and a braid cardioverting electrode.

U.S. Pat. No. 5,243,980 to Mehra, which is assigned to Medtronic, Inc., Minneapolis, Minn., discloses a lead system including a lead for use in the coronary sinus (CS) having two ring electrodes located for positioning within the atrium and intended for use in sensing and stimulating the atrium. According to an article by Bardy et al., entitled "Implantable Transvenous Cardioverter-Defibrillators," in Circulation, April 1993, vol. 87, no. 4, pp. 1152–1168, in five out of fifty patients (10%) receiving a CS lead provided by Medtronic, Inc., the lead dislodged; in three of the five patients, the CS leads would not stay in position despite reapplication. While this dislodgment rate may reflect the early phase of the physician learning curve, or the infancy of the lead design, it is much higher than the lead dislodgment rate of dual-chamber pacemakers (1–4%, as stated in the same article), which typically have one electrode in the right ventricle and one in the right atrium.

Minimizing the number of leads required by including atrial sensing electrodes on the defibrillator lead would reduce the implantation time and the amount of hardware residing in the patient's veins and heart. Also, especially for leads having silicone rubber insulation, placing a second lead often disturbs the placement of the first, since the lead body of the second lead tends to stick to the lead body of the first and drag it along. The problem is worse as more leads are added. Additionally, implantation is simplified with a straight lead having no branching lead body or electrodes.

SUMMARY OF THE INVENTION

The present invention provides a lead for use with an implantable cardioverter/defibrillator system in which defibrillation and atrial sensing electrodes are combined on the same lead. In the preferred embodiment, the lead system combines a right ventricular endocardial defibrillation electrode, a superior vena cava defibrillation electrode and one or more atrial sensing electrodes on a single catheter lead. As used herein to describe a location for lead placement, "superior vena cava" and "SVC" may refer to any location near the SVC, such as within the SVC, near or partially within the right atrium, or in the innominate vein. The distal end of the lead is transvenously implanted, typically through an incision in the subclavian or cephalic vein. The proximal end of the lead is then tunneled below the fascia to the abdominal or pectoral location of the pulse generator. Each of the two defibrillation electrodes may be of the coiled coil electrode type described in copending U.S. patent application Ser. No. 08/126619, filed Sep. 24, 1993 by Mar et al., for a "Flexible Defibrillation Electrode of Improved Construction" which is assigned to the assignee of the present application. However, other electrode types may be used. A pacing electrode may also be included at the distal end of the lead to provide ventricular sensing to detect arrhythmias and allow bradycardia and/or antitachycardia pacing.

In an alternative embodiment, the lead has only one defibrillation electrode. One or more atrial sensing electrodes are positioned on the lead in the atrial region.

It is thus an object of the present invention to provide a lead for an implantable defibrillator which exhibits improved atrial sensing.

In another embodiment of the invention, one or more atrial sensing electrodes is programmably paired with different ones of two or more defibrillation electrodes to provide alternative atrial sensing capabilities.

BRIEF DESCRIPTION OF THE DRAWINGS

The various features and advantages of the present invention may be more readily understood with reference to the following detailed description taken in conjunction with the accompanying drawings where like reference numerals are used to designate like elements and in which.

DETAILED DESCRIPTION OF THE INVENTION

Figure 1:
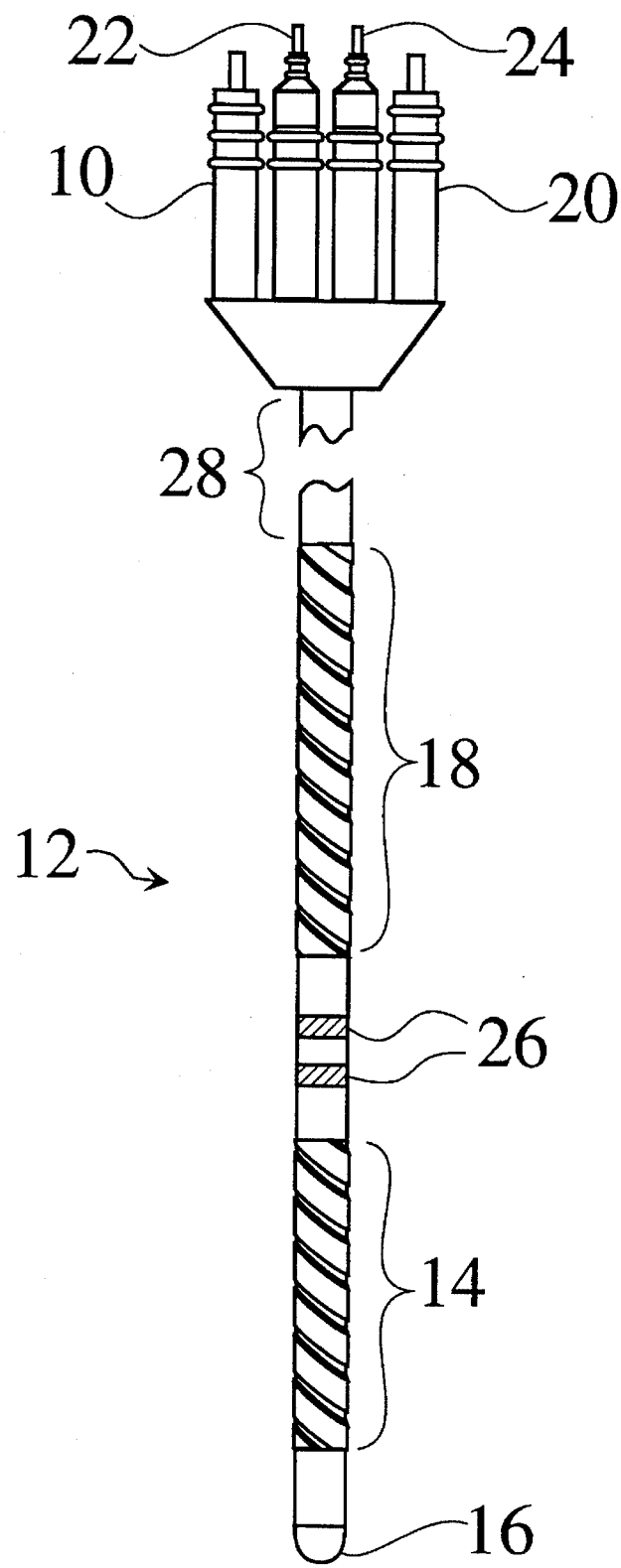
FIG. 1 illustrates the novel electrode arrangement of the present invention.

FIG. 1 shows the preferred embodiment of the transvenous implantable defibrillator lead of the invention. A pulse generator (not shown) such as the type described in U.S. Pat. No. 5,007,422 is implanted, typically within the abdominal region, and coupled with electrodes associated with the patient's heart. The pulse generator includes sensing and detecting circuitry, as well as pulse generating circuitry, coupled to the implantable electrodes. When an arrhythmic condition is sensed by the ICD, the ICD delivers cardioverting or defibrillating pulses to the heart through the implanted electrodes.

A catheter electrode arrangement is coupled to the ICD. A transvenous defibrillation lead 12 includes a right ventricular (RV) electrode 14 for positioning in the apex of the right ventricle. The RV electrode may be formed of a wound wire conductive spring electrode, of any construction known in the art. Other electrodes may be employed, such as ring-type electrodes. A superior vena cava (SVC) electrode 18 is positioned on the catheter proximal to the RV electrode. The SVC electrode is of the same spring electrode design used with the RV electrode. Alternatively, the SVC electrode may be a different type electrode than the RV electrode.

Two atrial sensing electrodes 26 are positioned between the RV electrode 14 and the SVC electrode 18, typically within about four centimeters of at least one defibrillation electrode 14 or 18 to ensure adequate bipolar sensing. The atrial sensing electrodes are used to sense signals such as P waves which initiate in the atria, to provide information to the defibrillator for discriminating atrial and ventricular rhythms. The atrial sensing electrodes may be of any of the ring-type electrodes known in the art, or of the construction described in U.S. Pat. No. 4,630,611 to King which uses three mutually orthogonal electrode pairs, or may be of any other construction.

The defibrillation lead 12 is inserted transvenously through an incision in a vein such as the cephalic or subclavian vein to a position such that the RV electrode 14 is positioned in the right ventricular apex of the heart and the SVC electrode is near the superior vena cava. The position of the SVC electrode is determined in part by its spacing along the catheter lead from the RV electrode, It is not required that it be positioned exactly within the superior vena cava and may be in the right atrium or the innominate vein. The lead includes an insulating catheter through which a plurality of conductors run to connect the electrodes to the pulse generator. After the electrodes are transvenously positioned in or near the patient's heart, the lead body 28 and connectors 10, 20, 22, and 24 (described below) of lead 12 are tunneled from the implant incision to the pulse generator. This is commonly done with a shaft which is passed beneath the fascia of the patient to the pocket where the pulse generator is positioned from the site where the vein is punctured. The RV electrode and SVC electrode may be internally coupled within the lead body or electrically connected to the pulse generator by separate conductors. Therefore, they may be of the same or opposite voltage polarity.

The lead may be secured in the RV apex with conventional fixation means (not shown) such as tines or a screw.

An RV pacing electrode 16 may be included on the distal end of defibrillation lead 12. The distal tip in conjunction with the RV electrode 14 provides sensing of the heart rate as well as antitachycardia and bradycardia pacing functions. Alternatively, RV pacing electrode 16 may be used to form a bipolar pair with an additional electrode (not shown) located between RV pacing electrode 16 and RV defibrillation electrode 14. However, this additional electrode, which may be a ring electrode of known construction, may complicate the lead mechanically, require an additional conductor, and necessitate a shorter RV defibrillation electrode length, and, consequently, smaller RV defibrillation electrode surface area.

Antitachycardia pacing is a method of terminating ventricular tachycardia by delivering a series of low energy pulses synchronized with the heart rhythm. Bradycardia pacing is used to increase an abnormally slow heart rate. Because they have no atrial electrodes, currently available defibrillation lead systems deliver this therapy as follows: the ventricle is stimulated, only the ventricle is used to sense heart rate, and the artificial pacemaker stimuli are inhibited by sensed natural beats; this is referred to as VVI pacing. In the system of the present invention which has atrial sensing electrodes, VDD mode can be used. In this mode, the ventricle is paced, both the ventricles and the atria are used to sense heart rate, and pacemaker stimuli can be both inhibited by sensed ventricular beats and triggered by atrial beats. VDD mode provides the benefit of AV synchrony, improving oxygen uptake, increasing work capacity, and improving heart rate and systolic blood pressure. The atrial electrodes also can be used to pace the atria, delivering bradycardia pacing therapy in DDD mode. A technique similar to that described in U.S. Pat. No. 3,825,015 to Berkovits can be used, where several axially spaced ring electrodes are carried on the catheter spaced so as to be located in the atrium; the two atrial electrodes providing best contact with the atrium are selected for use. This use of multiple atrial electrodes, and choosing the two best, also may be used to provide a means for optimizing sensing.

The proximal end of the defibrillation lead 12 may include connectors 10, 20, 22, and 24 for connection to the pulse generator. Connectors 10 and 20 are shown for connection of the RV and SVC defibrillation electrodes, respectively, and are both required if these electrodes are of opposite polarity. However, only one defibrillation connector is needed if they are of the same polarity and internally coupled in the lead. Connectors 22 and 24 are for the ventricular sensing and pacing, and the atrial sensing (and pacing if used), respectively.

A subcutaneous patch electrode (not shown) may be positioned outside the rib cage and either above or below the muscles of the left chest wall. The pulse generator case may be active or inactive; that is, it may or may not act as a defibrillation electrode. An epicardial defibrillation electrode may occasionally be used, for example, in patients who have very high thresholds with the other less invasive lead configurations.

Figure 2:
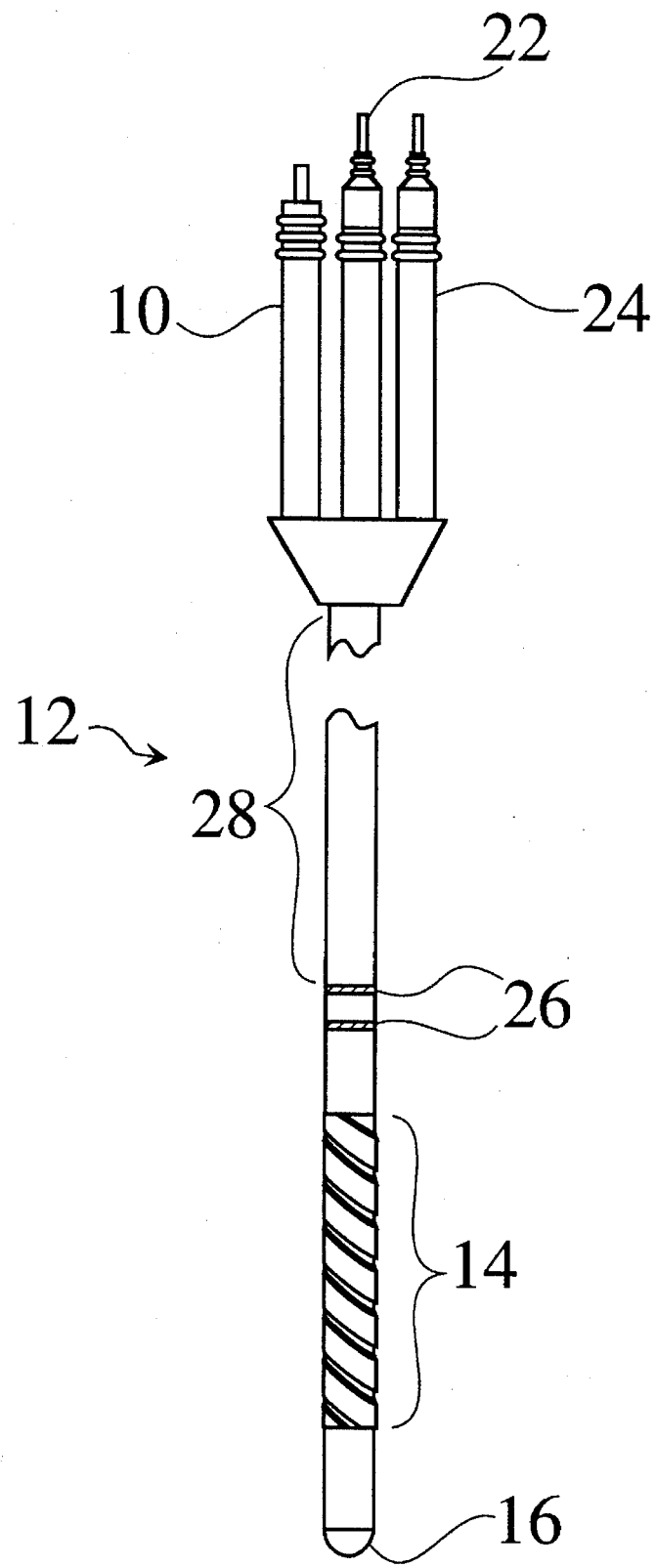
FIG. 2 illustrates an alternative embodiment of the invention having an RV defibrillation electrode and atrial sensing.

FIG. 2 shows a transvenous defibrillation lead 12 having an RV electrode 14 and at least one atrial sensing electrode 26. When only one atrial sensing electrode is included, the other electrode used to form a pair for atrial sensing may be a pulse generator case that is active for sensing, a subcutaneous patch electrode, an epicardial electrode, an SVC electrode on a second transvenous lead, or the RV electrode 14. In the case where the RV electrode 14 is used, the sensed signal may appear more like a surface electrocardiogram (ECG) than a signal obtained solely from the atria. In the case where the pulse generator case, subcutaneous lead, or epicardial lead is used, the signal may be more similar to the signals obtained using "unipolar" atrial pacing leads. When an SVC electrode or at least one additional atrial sensing electrodes is used, the signal should appear the same as signals obtained from "bipolar" atrial pacing leads, since the electrode spacing is closer, and the electrodes are confined to the atria or above. If a "bipolar" rather than a "unipolar" signal is desired, it is recommended that the electrodes forming the bipole be spaced within about two centimeters of each other, and preferably within about one centimeter of each other.

To implant the lead of FIG. 2, the distal end of the transvenous lead 12 which carries RV electrode 14 is fed through an incision in the cephalic or subclavian vein to a position such that the RV electrode 14 is positioned in the right ventricular apex of the heart. At this point, the atrial sensing electrodes 26 should be positioned in the region of the atria. Once the electrodes are positioned, the proximal end of the transvenous lead 12, which includes connectors 10, 22, and 24 for connection to a pulse generator, is then tunneled from the implant incision to the pulse generator.

The lead of FIG. 2 may be used for defibrillation with any combination of the following: a second transvenously placed defibrillation lead, a subcutaneous patch electrode, and an active pulse generator case. Alternatively, the lead of FIG. 2 could be used with other known electrodes such as epicardial patch electrodes.

A distal pacing electrode 16 may be included on the catheter of transvenous lead 12. The distal tip in conjunction with the RV electrode 14 provides sensing of the heart rate as well as pacing functions. This pacing tip may be of any of the numerous constructions known in the art.

Figure 3:
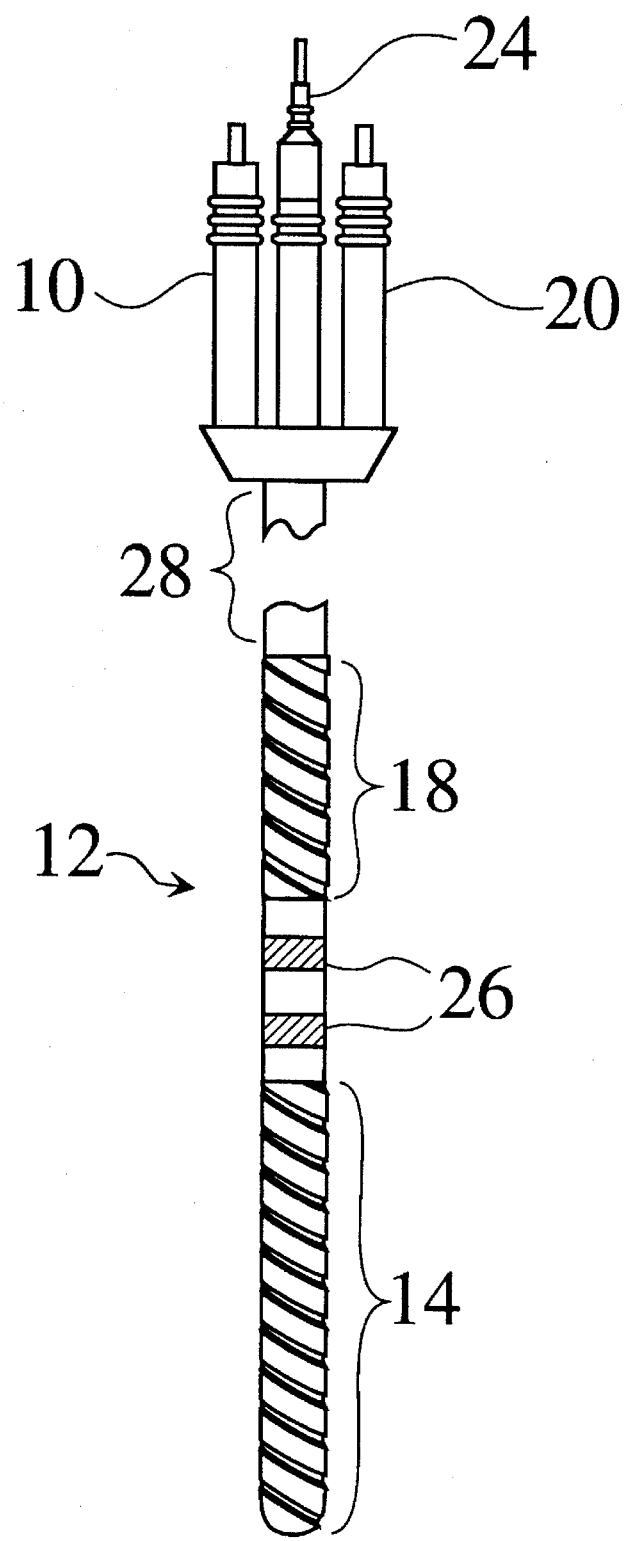
FIG. 3 illustrates a lead which requires a separate electrode for ventricular sensing and pacing.

FIG. 3 shows a lead having an RV defibrillation electrode 14 and an SVC defibrillation electrode 18, and two atrial sensing ring electrodes 26, but no distal pacing tip electrode. Other lead configurations having no distal pacing electrode are possible, including a lead with only one defibrillation electrode and/or one atrial sensing electrode, or a lead with more than two defibrillation electrodes and/or more than two atrial sensing electrodes. When using this lead, an additional lead having pacing and sensing electrodes would be required in the RV for bradycardia and antitachycardia pacing and for bipolar sensing of the intracardiac electrograms. One reason for excluding a pacing electrode from this embodiment is to bring the RV electrode 14 closer to the myocardium, and to maximize the defibrillation electrode length available to increase the defibrillation surface area. (This length is limited since the RV defibrillation electrode should not extend through the tricuspid valve.) Another reason is to decrease complexity of the lead, decrease the number of conductors and insulators required, and in turn decrease lead diameter. Yet a third reason is to allow the implanting physician to optimize lead placement for defibrillation and atrial sensing independent of optimal placement of bradycardia and antitachycardia pacing and ventricular sensing.

Figure 4:
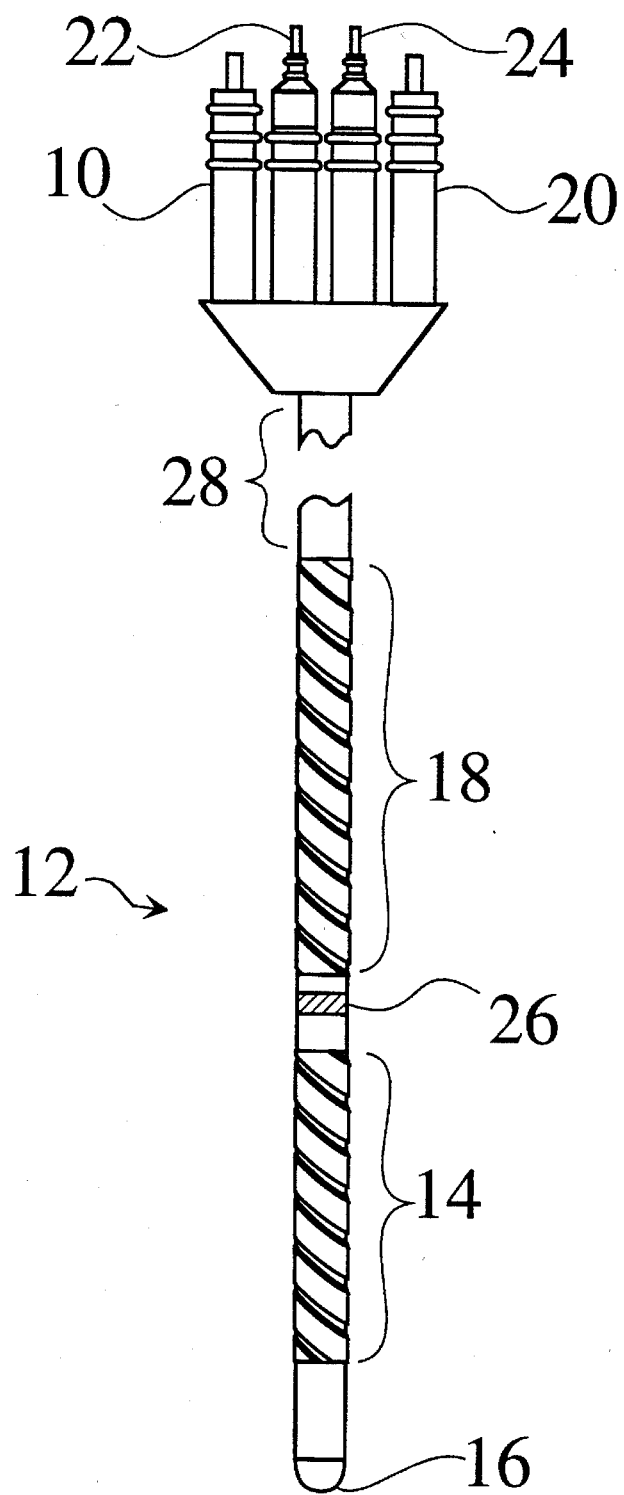
FIG. 4 illustrates a lead having an RV and SVC defibrillation electrode, and only one atrial sensing ring electrode which is coupled with the SVC electrode for bipolar atrial sensing.

FIG. 4 shows a lead having RV electrode 14 and SVC electrode 18, and only one atrial sensing ring electrode 26 which is coupled with the SVC electrode 18 for bipolar atrial sensing. In this way, the number of electrical connections, conductors, and insulators is decreased from the embodiment of FIG. 1. The atrial sensing electrode 26 may alternatively be coupled with another electrode in the system, as described in connection with FIG. 2 above and FIG. 5 below. The system may be programmable to allow a choice of which electrode will be used to form the bipolar pair with the atrial sensing electrode. The system may also be programmable for sensing parameters and/or algorithms used to discriminate between various arrhythmias, depending on which electrode combination is chosen for the bipolar sensing pair. This allows the sensing electrodes and function to be optimized for each patient.

"An RV pacing electrode 16 may be included on the distal end of defibrillation lead 12. The distal tip in conjunction with the RV electrode 14 provides sensing of the heart rate as well as antitachycardia and bradycardia pacing functions. Alternatively, RV pacing electrode 16 may be used to form a bipolar pair iwth an additional electrode (not shown) located between RV pacing electrode 16 and Rv defibrillation electrode 14."

Figure 5:
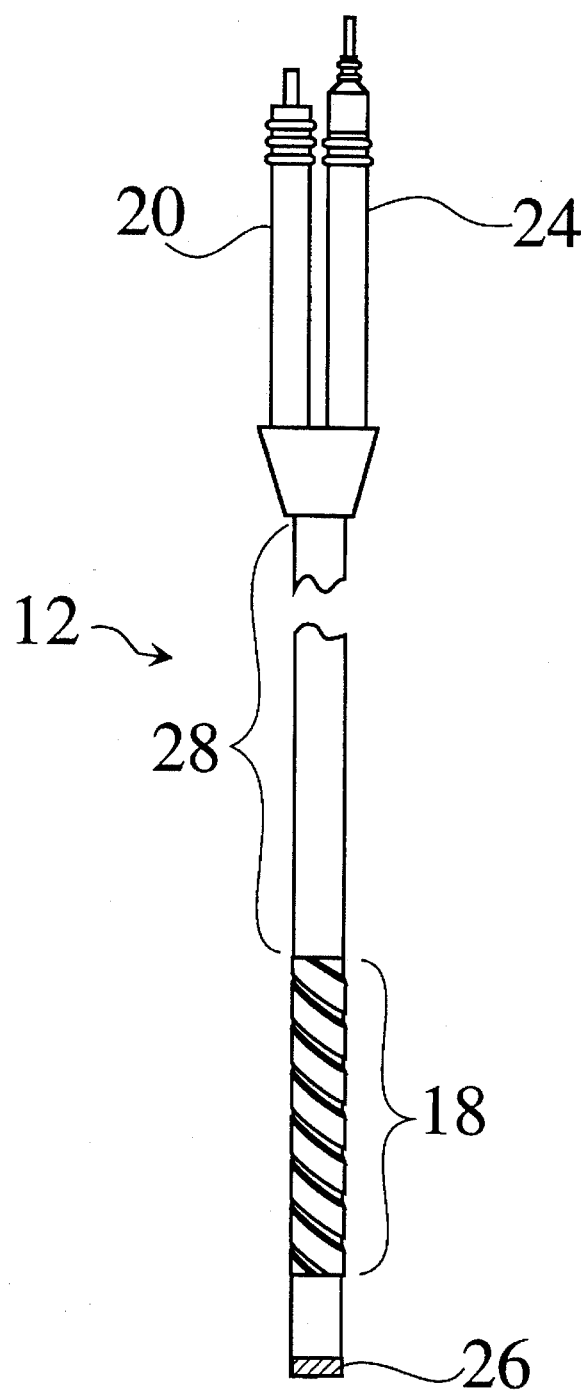
FIG. 5 illustrates a lead having an SVC defibrillation electrode and atrial sensing.
Figure 6:
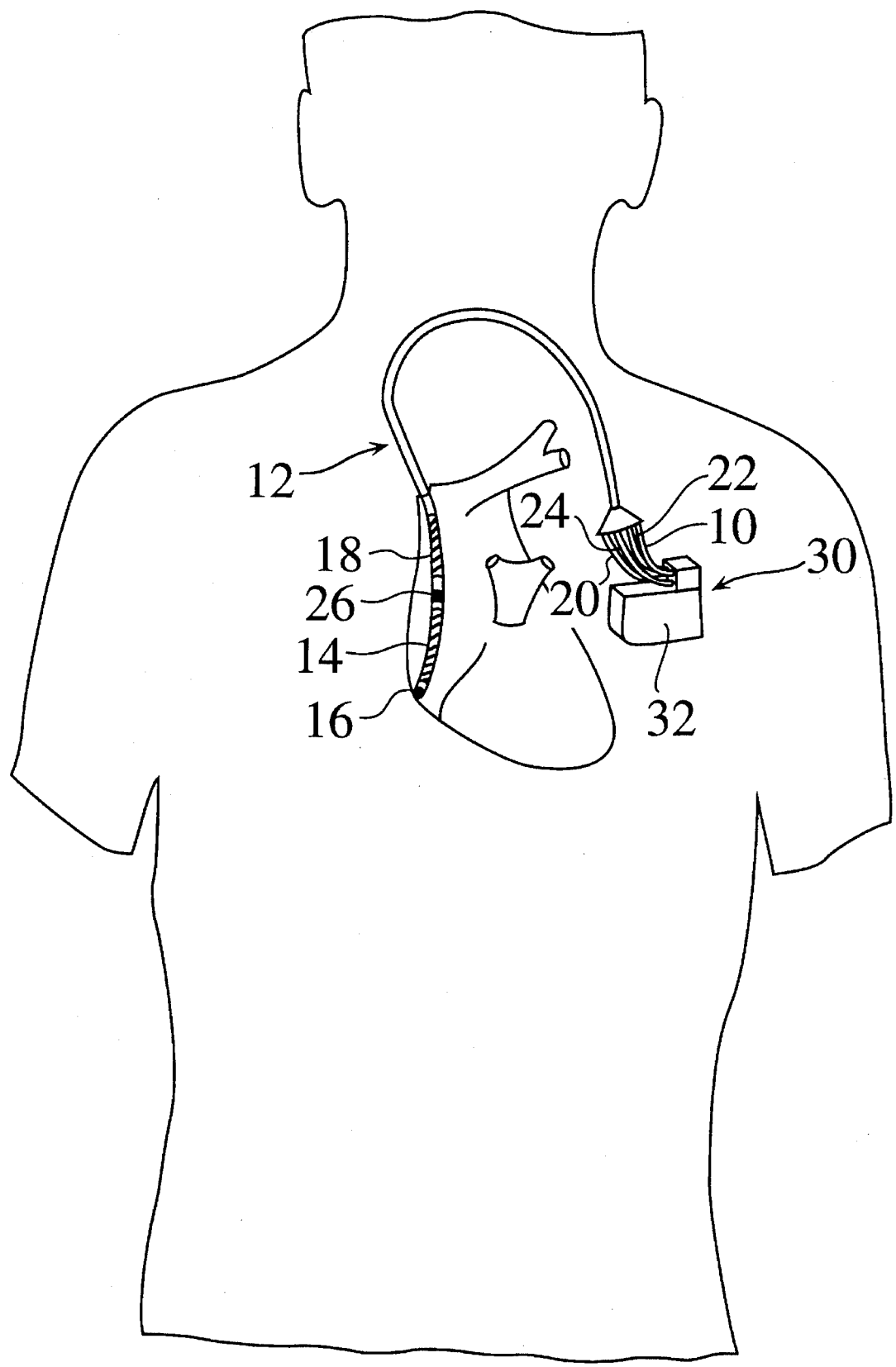
FIG. 6 illustrates an implantable defibrillator system having an electrical connection of the electrodes 16, 14, and 26, and 18 of lead 12 to pulse generator 30. Pulse generator 30 has a case 32 which may be used as a defibrillation electrode instead of or in addition to defibrillation electrode 18 or 14, and which may be paired with atrial sensing electrode 26 for atrial sensing. Electrode 26 is electrically connected to the sensing circuitry of pulse generator 30 via a sensing connector 24. A second electrode 14, 18, or 32 is also electrically connected to the sensing circuitry of pulse generator 30, either via sensing connector 24 (for electrode 14 or 18) or directly (for electrode 32, which is the case of pulse generator 30) thereby forming an electrode pair for atrial sensing.

FIG. 5 illustrates a defibrillation lead 12 having an SVC electrode 18 such as the one described in connection with FIG. 1 above. It also has one atrial sensing electrode 26. This electrode 26 can be used to form a pair for atrial sensing with a pulse generator case that is active for sensing, a subcutaneous patch electrode, an RV electrode on a second transvenous lead, or the SVC electrode 18. As described in connection with FIG. 2 above, when using the atrial sensing electrode in conjunction with an active case or a patch electrode, the signal will be similar to that from a "unipolar" atrial pacing lead; with the RV electrode, the signal will be similar to that from a surface ECG; and using the SVC electrode will provide signals mainly from the atria, similar to those from a "bipolar" atrial pacing lead.

It will be apparent from the foregoing description that the lead of this invention provides for significant improvement in arrhythmia sensing for an implantable cardioverter defibrillator without added complexity in the implantation.

It should be understood that various alternatives to the embodiments of the invention described herein may be employed in practicing the invention. It is thus intended that the following claims define the scope of the invention and that structures and methods within the scope of these claims and their equivalents be covered thereby.

What is claimed is:

1. A defibrillation lead for use in a patient with an implantable defibrillator comprising:
   a catheter having a proximal end and a distal end, said catheter having at least one defibrillation electrode for placement through a vein and in said patient's right ventricle:
   at least one atrial sensing electrode positioned on said catheter for placement proximate said patient's atria;
   a second defibrillation electrode positioned on said catheter toward said proximal end relative to said at least one atrial sensing electrode for placement proximate said patient's superior vena cava; and
   at least one connector at said proximal end of said catheter for electrically connecting said electrodes to said implantable defibrillator.

2. A defibrillation lead according to claim 1 and further including a pacing electrode positioned on said distal end of said catheter.

3. A lead for use in a patient with an implantable defibrillator comprising:
   a catheter having a proximal end and a distal end, said catheter having a first defibrillation electrode for placement through a vein and proximate said patient's superior vena cava;
   one atrial sensing electrode positioned on said catheter for placement proximate said patient's atria and toward said distal end relative to said first defibrillation electrode, said atrial sensing electrode forming a bipolar electrode pair with said defibrillation electrode for atrial sensing;
   a second defibrillation electrode positioned toward said distal end relative to said atrial sensing electrode for placement in said patient's right ventricle; and
   at least one connector at said proximal end of said catheter for electrically connecting said electrodes to said implantable defibrillator.

4. The lead of claim 3 wherein said atrial sensing electrode is a ring electrode.

5. The lead of claim 3, and further including a pacing electrode positioned on said catheter toward said distal end relative to said second defibrillation electrode for placement in said patient's right ventricle.

6. A defibrillation lead for use in a patient with an implantable defibrillator comprising:
   a catheter having a distal end and a proximal end, said catheter having a first defibrillation electrode positioned near said distal end for placement through a vein and into the right ventricle of said patient's heart;
   a second defibrillation electrode positioned on said catheter toward said proximal end relative to said first defibrillation electrode;
   at least one sensing electrode positioned on said catheter between said first and second defibrillation electrodes; and
   a connector at the proximal end of said catheter for electrically connecting said electrodes to an implantable defibrillator.

7. A defibrillation lead according to claim 6 and further including a pacing electrode positioned on said distal end of said catheter.

8. An implantable cardioverter/defibrillator system for delivering electrical discharges to a patient's heart to restore normal cardiac rhythm comprising:
   a pulse generator for generating an electrical shock;
   a lead having a distal end and a proximal end and at least one defibrillation electrode for placement through a vein and in said patient's right ventricle for connection to said pulse generator;
   at least one atrial sensing electrode positioned on said lead, spaced from said defibrillation electrode by about four centimeters or less, for placement proximate said patient's atria, said lead being essentially straight and unbranched; and
   means for electrically connecting said electrodes to said pulse generator.

9. The defibrillator system of claim 8, wherein said defibrillation electrode is located toward said distal end relative to said atrial sensing electrode for placement in said patient's right ventricle, and further including a second defibrillation electrode positioned on said lead for placement proximate said patient's superior vena cava.

10. The defibrillator system of claim 8, wherein said means for electrically connecting said electrodes to art implantable defibrillator comprises first and second sensing connectors, and wherein said atrial sensing electrode is electrically connected to said first sensing connector and said defibrillation electrode is electrically connected to said second sensing connector thereby forming an electrode pair for atrial sensing.

11. The defibrillator system of claim 10, wherein said defibrillation electrode is located toward said distal end relative to said atrial sensing electrode for placement in said patient's right ventricle.

12. The defibrillator system of claim 8, and further comprising a ventricular pacing electrode positioned on said distal end of said lead.

13. The defibrillator system of claim 8, wherein said atrial sensing electrode is a ring electrode.

14. The defibrillator system of claim 8, wherein said pulse generator includes a case which is adapted for use as an electrode, and wherein said atrial sensing electrode is connected to said pulse generator by a first sensing connector and wherein said pulse generator case and said first sensing connector are electrically connected to form an electrode pair for atrial sensing.

* * * * *